United States Patent [19]

Bloxom, Jr.

[11] Patent Number: 4,769,015
[45] Date of Patent: Sep. 6, 1988

[54] MOUNTING ASSEMBLY FOR INTESTINAL IRRIGATION APPARATUS

[76] Inventor: Ingrid B. Bloxom, Jr., P.O. Box 357, Wicomico, Va. 23184

[21] Appl. No.: 858,102

[22] Filed: May 1, 1986

[51] Int. Cl.$^4$ .......................................... A61M 31/00
[52] U.S. Cl. .................... 604/277; 604/257; 604/27; 248/125; 248/215; 248/159
[58] Field of Search ............. 604/27, 35, 277, 408, 604/257; 248/125, 215, 207, 244–246, 297.2, 159

[56] References Cited

U.S. PATENT DOCUMENTS

| | | | |
|---|---|---|---|
| 2,036,218 | 4/1936 | Kammer | 604/27 |
| 2,257,072 | 9/1941 | Coombs | 604/35 |
| 2,677,519 | 5/1954 | Hobson | 248/125 |
| 3,168,200 | 2/1965 | Larson | 248/125 |
| 3,830,235 | 8/1974 | Marsan | 604/277 |
| 4,030,690 | 6/1977 | Hanauer et al. | 248/125 |
| 4,088,166 | 5/1978 | Miller | 604/408 |
| 4,387,873 | 6/1983 | Paulo et al. | 248/215 |
| 4,405,109 | 9/1983 | Murdoch | 248/215 |
| 4,425,123 | 1/1984 | DiSalvo | 604/257 |
| 4,461,387 | 7/1984 | Belokin, Jr. | 248/159 |
| 4,518,382 | 5/1985 | Bloxom, Jr. | 604/257 |
| 4,617,011 | 10/1986 | Bloxom, Jr. | 604/27 |
| 4,698,054 | 10/1987 | Bloxom, Jr. | 604/54 |

FOREIGN PATENT DOCUMENTS 2029197  3/1980  United Kingdom ............ 248/297.2

Primary Examiner—Stephen C. Pellegrino
Assistant Examiner—Ralph Lewis
Attorney, Agent, or Firm—John Cyril Malloy

[57] ABSTRACT

A mounting assembly for use in the adjustable supporting of various components of a colonic irrigation or flushing apparatus of the type which directs irrigating fluid, by gravity flow, through a flow monitoring device and therefrom through appropriate conduit to an introduction element which is designed to be inserted in the colon entrance for direct delivery of irrigating fluid thereto. The mounting assembly includes an elongated base having a plurality of connecting elements on which various components, such as the supply container and monitoring device are supported and further, wherein the connecting elements are structured for selective movement and placement thereof along the length of the base so as to properly position the supply container, monitoring device and depending conduit and introduction element in a preferred location relative to one another and the user of the apparatus being treated.

7 Claims, 4 Drawing Sheets

MOUNTING ASSEMBLY FOR INTESTINAL IRRIGATION APPARATUS

BACKGROUND OF THE INVENTION

1. Field of the Invention

A mounting assembly capable of being temporarily positioned or substantially permanently installed and specifically structured to support a colonic irrigation apparatus in a manner which allows a supply container and monitoring device thereof to be adjustably positioned in a relative vertical orientation to one another and to the user of the apparatus during the irrigation process.

2. Description of the Prior Art

Colonic irrigation is a well known medical treatment and is utilized not only in the case of conventional enemas wherein irrigating fluid is introduced through the anis end of the rectum, but also in the case of irrigation through surgically provided openings into other parts of the colon. Such is the case in colostomy patients. In providing such irrigation or flushing treatment, for the purpose of evacuating fecal matter, the degree of discomfort and length of the ordeal, using certain prior art apparatus and techniques is significant.

Prior art treatment has been found to be particularly disagreeable for those requiring irrigation of the intestine directly into the colon through the aforementioned surgically provided opening referred to herein as the stoma. Such stomas are formed from the end of a shortened colon after the end has been secured to a opening in the stomach wall and anchored to the stomach wall for clear access thereto.

Prior art equipment designed to introduce irrigating fluid into the colon of a colostomy patient is disclosed, for example, in U.S. Pat. No. 3,830,235 to Marsan. Such equipment conventionally includes a supply bag or container for irrigating fluid, a flexible tube or conduit to convey liquid from the bag to the stoma by means of a stoma cone or introduction device through which liquid is directly applied into the colon; a clip or like structure to regulate flow of irrigating fluid through the tube and a discharge device to catch the backflow of evacuated fecal matter when the cone is removed from the stoma.

While prior art equipment in systems of the type described above are operable to accomplish flushing or evacuation of the colon, prior art systems of the type referred to above are generally recognized, especially by patients having colonical treatment, as having certain disadvantages. Such disadvantages relate not only to the degree of discomfort and length of time to accomplish such treatment but also to the proper mounting or placement of the flushing apparatus by what may be referred to as auxiliary equipment. Such equipment is used to support the irrigating apparatus so that the patient may accomplish the intended operation of the irrigating apparatus in the most efficient manner.

Preferably, such auxiliary equipment includes a mounting assembly capable of movably and/or adjustably mounting and positioning various components of the irrigating assembly, namely the supply container and a monitoring device, in proper position relative to one another and at a level, relative to the patient or user of the apparatus which accomplishes the most effective operation of the irrigating apparatus. The irrigating apparatus or device referred to hereinafter is preferably of the type of irrigating apparatus disclosed and claimed in U.S. Pat. No. 4,518,382. Utilizing such equipment, it should be apparent that the supply container should be properly positioned for allowing gravity flow of the irrigating liquid therefrom through a flexible conduit to a monitoring device or apparatus. The monitoring device of the type referred to in the above noted patent should be properly positioned and in some embodiments horizontally oriented for easy detection of information relating to the direction of flow of the irrigating liquid and the development of peristaltic action in the intestine being irrigated. Further, both of the aforementioned components of the irrigating assembly should be properly positioned so as to allow depending orientation of the remaining portion of the conduit and the introduction element or stoma cone attached to the distal extremity thereof.

SUMMARY OF THE INVENTION

The present invention relates to a mounting assembly for a colonic irrigation apparatus specifically of the type including a supply container of irrigating fluid required to be positioned vertically above the point of introduction of the irrigating fluid into the colon. The subject irrigating apparatus further includes a monitoring device structured to indicate conditions of fluid flow of the irrigating fluid as it passes from the supply container through a flexible conduit to the monitoring device and outwardly therefrom along additional conduit structure. The irrigating fluid is then channeled through an introducing element such as a stoma cone or like structure positioned directly into the stoma or other entrance to the colon, such as the anis.

More particularly, the mounting assembly of the present invention includes an elongated base having a track or like guide means formed substantially along a major portion of the length of the base. A plurality of connecting elements, preferably at least two, are structured so as to be fixedly positioned at selected locations along the length of the base and more specifically the length of the track means. The track means and each of the connecting elements are cooperatively structured to allow linear travel of the various connecting elements along predetermined portions of the base or track means. This in turn allows selective and preferred placement of each of the components, such as the supply container and monitoring device in spaced relation to one another but at a specific level or height relative to the user or patient undergoing the irrigating process. Therefore, the structure of the present invention allows for either one or both of the aforementioned components of the irrigating apparatus to be selectively positioned and then readjusted for proper positioning. For example, it may be desired to locate the supply container at eye level and locate the monitoring device in spaced relation thereto below the supply container so as to monitor direction of flow of the irrigating liquid for determination of the development of peristaltic action within the intestine.

Support means are provided for the supporting of the base in an upright substantially vertically oriented position. This facilitates the vertical disposition of the supply container over the monitoring device at a certain height relative to the point of introduction of the irrigating fluid into the colon or intestine being irrigated. The support means associated with the base may include a number of different embodiments such as a hooked shape bracket secured to an uppermost end of the base for removably supporting the base as well as the supported components of the irrigating apparatus on a horizontally disposed shower rod or like structure.

The support means may also take the form of a support platform removably secured to the lowermost end of the base and being of sufficient dimension and configuration to rest on a horizontal supporting surface. This serves to maintain the base in the aforementioned preferred upright position. Additionally, the support means may include one or more connector elements passing through preformed apertures in each of the opposite ends of the base so as to secure the base to a wall surface or the like in a substantially permanent fashion.

Another feature of the present invention is the ability to "break down" the base enabling it to be stored in a relatively small area or easily carried with the person or patient during travel.

The invention accordingly comprises the features of construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 2 is a front plan view of the mounting assembly of the present invention with one embodiment of a support structure therefor.

FIG. 3 is a front plan view of another embodiment of the support structure for maintaining the mounting assembly in a substantially upright orientation.

FIG. 4 is a front plan view of yet another embodiment of the mounting assembly being secured to a wall structure or the like.

Like reference numerals refer to like parts throughout the several views of the drawings.

DETAILED DESCRIPTION OF THE PREFERRED EMBODIMENT

Figure 1:
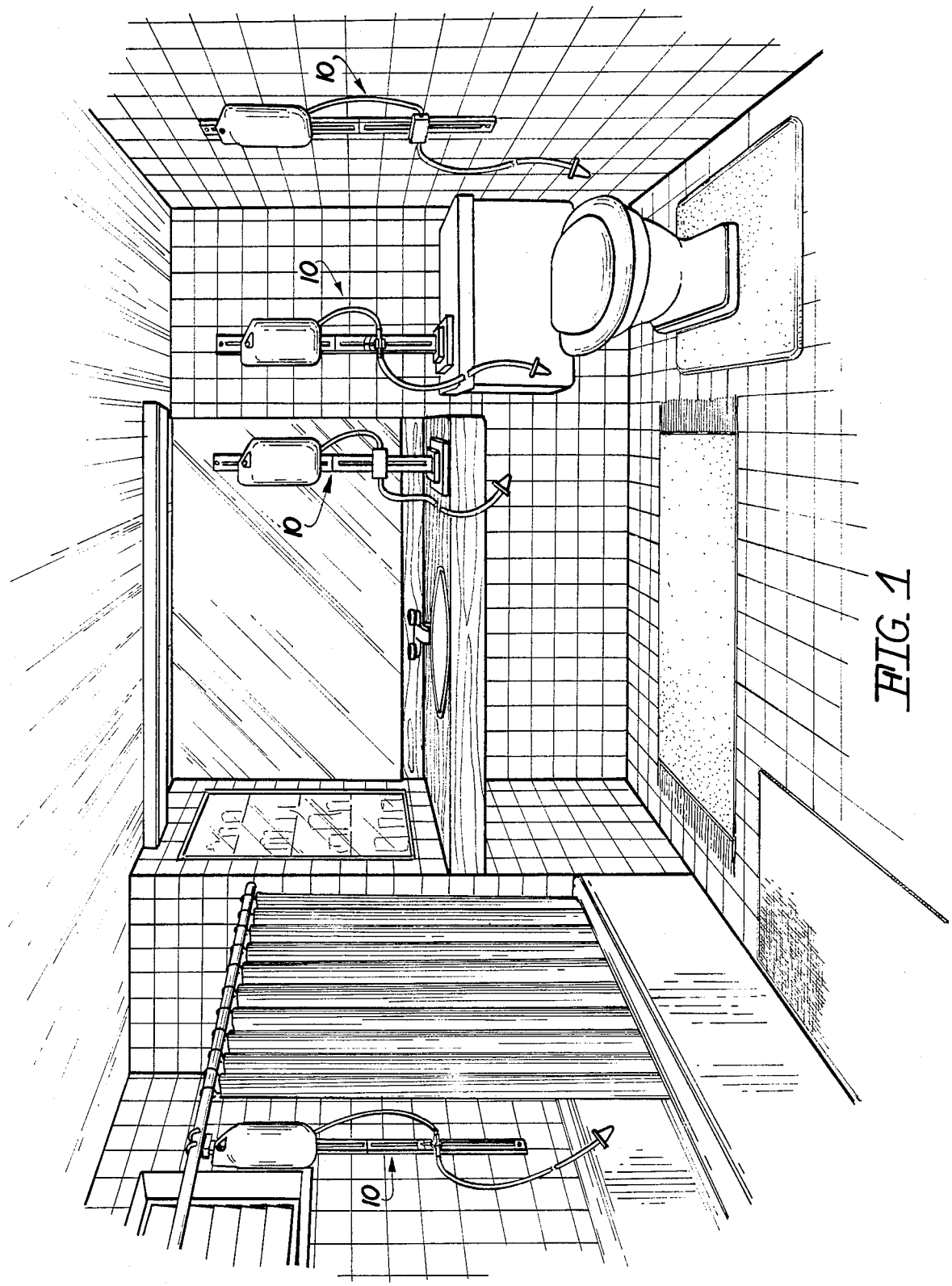
FIG. 1 is a perspective view of various locations in a conventional bathroom or like area in which various embodiments of the mounting assembly of the present invention and supported irrigating apparatus may be placed.

As shown in FIG. 1, the mounting assembly of the present invention is designed for support and placement of a colonic irrigation assembly in a variety of locations such as in a bathroom. A review of FIG. 1 shows three different embodiments of the mounting assembly 10 differing primarily in the embodiment of the support means of the present invention which serves to connect or securely position the mounting assembly 10 in a desired location for available use when a patient or user undergoes the flushing process. It should be evident that four different placements of the mounting assembly 10 are shown for purposes of explanation and in the typical home environment, only one of such mounting assemblies would be utilized at a time. It should further be noted that while the disclosure of FIG. 1 relates to placement of the mounting assembly and supported irrigating apparatus in a bathroom, the flushing process could take place at other locations. However, sanitary conditions dictate that the bathroom or like facility could be the best location.

Figures 2, 3, 4:
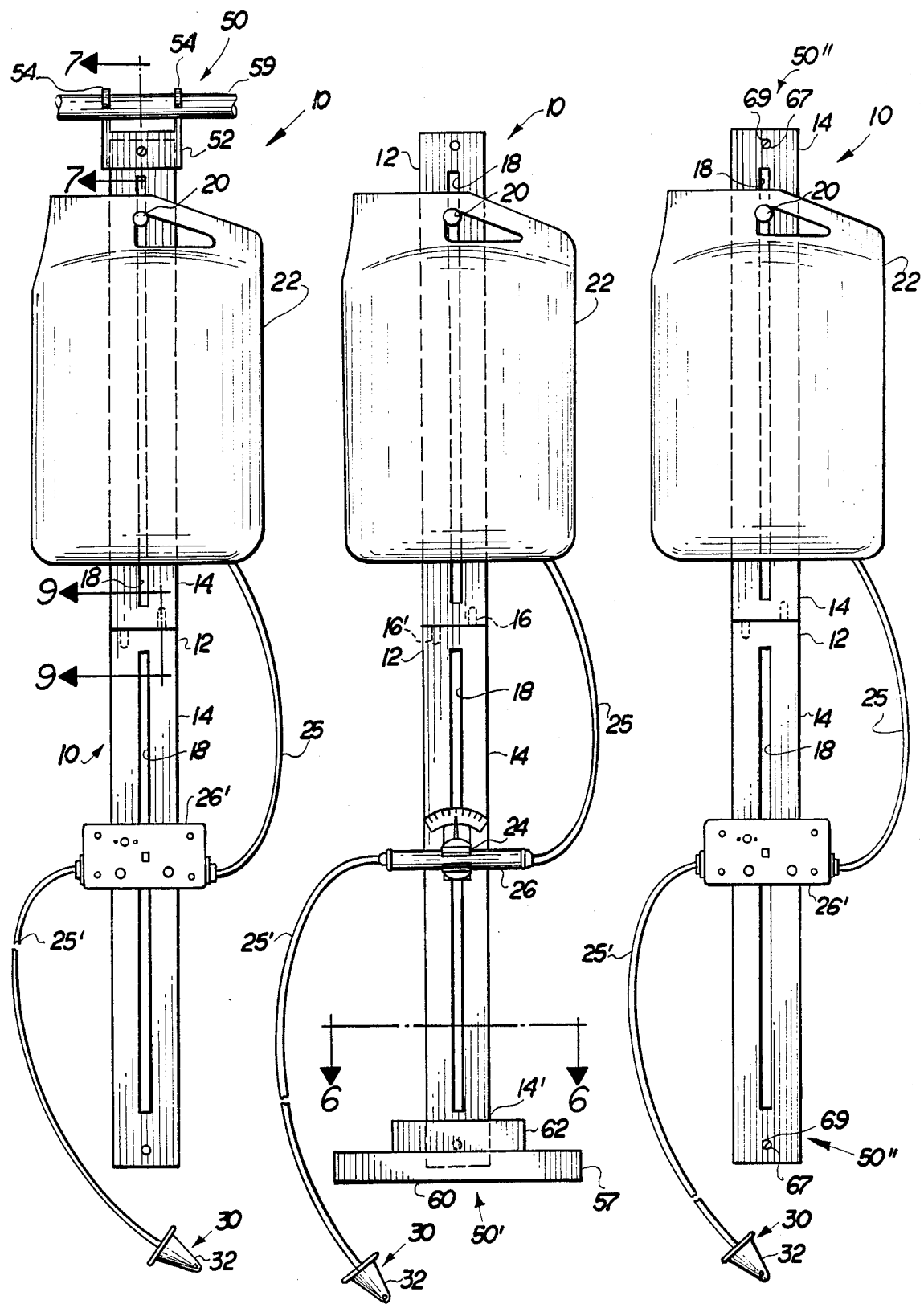
Figure 9:
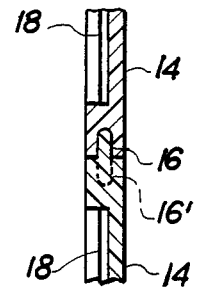
FIG. 9 is a sectional view in partial cutaway along line 9—9 of FIG. 2.

With reference to FIGS. 2, 3 and 4, the mounting assembly 10 shown therein differs only in the support means, to be described in greater detail hereinafter, attached thereto for upright, substantially vertical orientation of the base or standard 12. The base includes, in a preferred embodiment, a segmented construction including separable base segments 14 secured to one another in an end-to-end, colinear relation. While the connection between the base segments 14 may include a variety of different structures, in the embodiment shown, a pair of fingers 16 and 16' are integrally formed to extend out of correspondingly positioned and mating ends of the base segments 14 for frictional, mating engagement with a correspondingly positioned slot. The relative sizes of the fingers 16 and 16' and the slots in which they are mounted are such as to cause frictional engagement sufficient to maintain the two base segments 14 in their attached position as shown in FIGS. 3 and 9.

Figure 7:
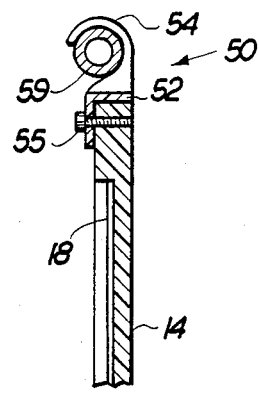
FIG. 7 is a sectional view in partial cutaway along lines 7—7 of FIG. 2.

The base generally and more specifically the base segments 14 each include a guide means in the form of an elongated track 18 formed in and extending along the length of each base segment 14. In a preferred embodiment, each of the track segments 18 include an integrally formed channel that may extend completely through or as shown in FIGS. 7 and 9 at least into the interior of the respective base segments 14 as shown in FIG. 7.

The guide means in the form of elongated tracks or track segments 18 are defined by integrally formed channels and are specifically structured and disposed along the length of each of the respective base segments 14 so as to movably contain and at least partially support connecting elements. The connecting elements include a first connecting element 20 for adjustably mounting a supply container 22, being as part of the irrigating apparatus, and a second connecting element 24 and 24' (see FIGS. 3 and 8) for adjustably mounting the monitoring device 26 along the length of the base segment 14. It will be noticed that the irrigating apparatus, for which the mounting assembly 10 of the present invention is designed to adjustably support, is of the type disclosed in U.S. Pat. No. 4,518,382 (see FIG. 3) and U.S. Pat. No. 4,617,011.

Figure 10:
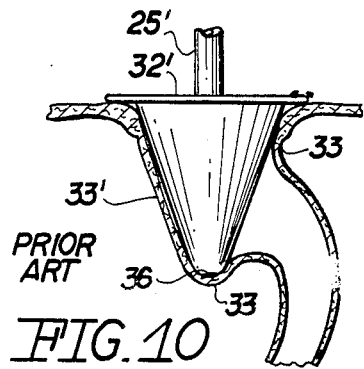
FIG. 10 is a sectional view in partial cutaway of a prior art introducing element or stoma cone.
Figure 11:
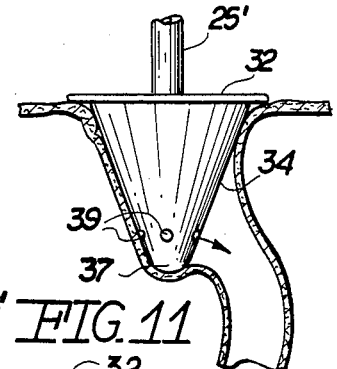
FIG. 11 is one embodiment of an introducing element or stoma cone associated with the irrigating apparatus of the present invention.
Figure 12:
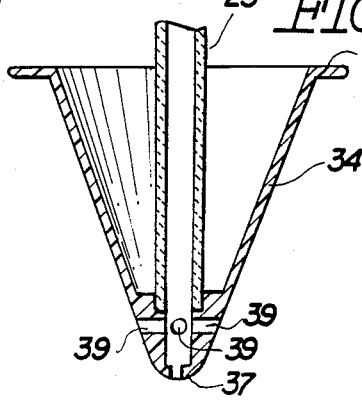
FIG. 12 is a detailed sectional view in partial cutaway of the embodiment of FIG. 11.

More specifically, the subject irrigating apparatus includes the supply container 22 designed to hold a preestablished amount of irrigating liquid. A conduit 25 extends from the supply container 22 and channels the irrigating fluid, due to gravity flow, to the monitoring device 26. In the embodiments of FIGS. 2 and 4, the monitoring device may be defined as an electronic monitoring device and indicated as 26' which is disclosed and claimed in the above-referenced patent to the inventor herein. A second conduit 25' or a continuation of the conduit 25 extends downwardly in depending relation from the monitoring device, 26, 26' and terminates in an introduction means generally indicated as 30. The introduction means 30 is preferably in the form of an introducing element 32 more specifically shown in FIGS. 11 and 12 and may generally be termed a stoma cone. With reference to FIGS. 10, 11 and 12, FIG. 10 represents what may be referred to as a prior art introducing structure 32' wherein the conduit 25', again due to gravity flow, directs the irrigating fluid into the interior of the prior art cone 32'. It is there intended to flow into the intestine entrance or opening 33 so as to enter the colon 34 as shown. However, after repeated usage of an irrigating apparatus and the repeated introduction of an introducing element or stoma cone 32', it is common for the surgically formed entrance 33 or stoma to become somewhat slightly deformed or less resilient causing a deformation of the leading portions of the colon being irrigated as at 33'. Accordingly, in the prior art structure 32', a distal aperture is integrally formed in the extremity as at 36 of the stoma cone 32'. Due to the location of this distal extremty 36 and the deformation of the leading portion of the colon 33', the irrigating fluid is totally or partially blocked from entering the interior of the colon 34 due to the referred to deformation.

Accordingly, in the present invention the introducing element or stoma cone 32 has a smooth exterior surface 34 terminating in a tip or distal end 37 which has spaced thereabove a plurality of channels 39. With reference to FIG. 12, conduit 25' directs irrigating fluid into the interior of the cone 32 and directly to the plurality of channels 39. Accordingly, even if a portion of the distal tip 37 of the stoma cone 32 is partially enveloped or blocked, there would still be at least a number of the plurality of channels 39 free to introduce the irrigating liquid into the interior of the colon as best shown in FIG. 11.

Figure 5:
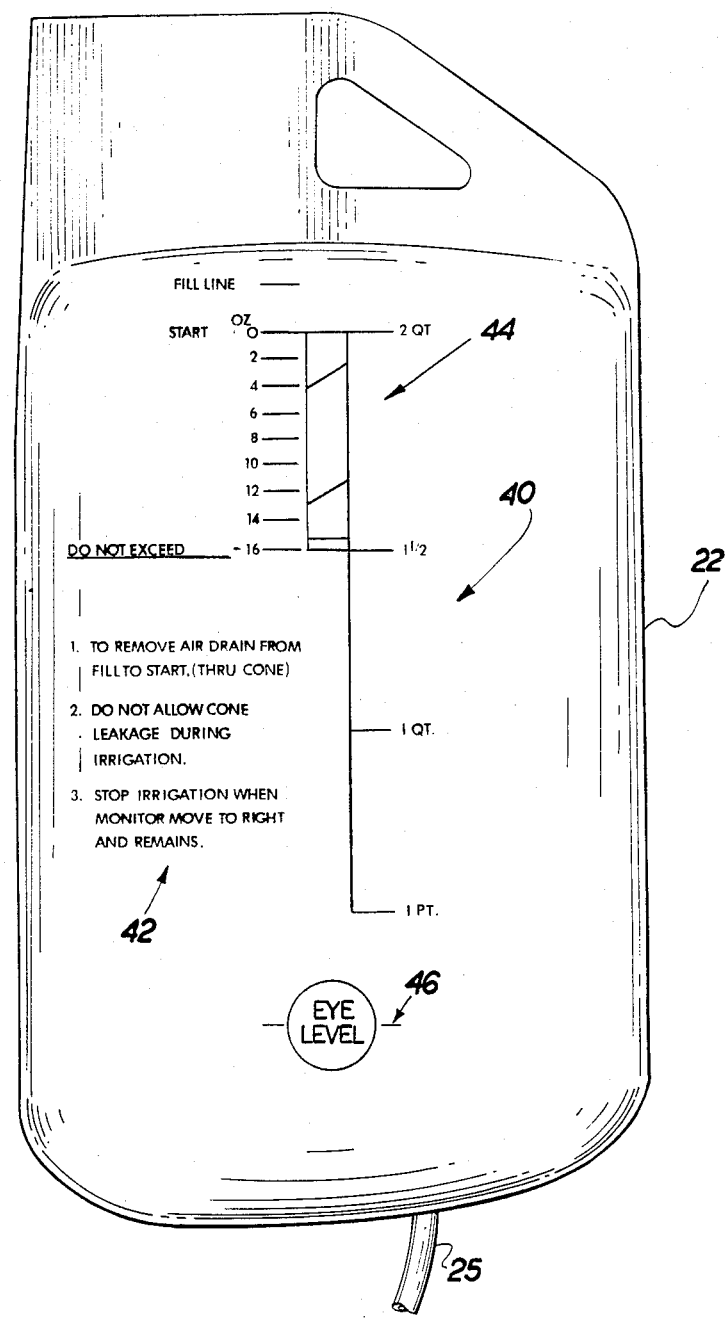
FIG. 5 is a detailed front plan view in partial cutaway showing instructional indicia and indicating structure formed on the supply container of the irrigating apparatus.

Other features of the irrigating apparatus used in combination with the subject mounting assembly comprises informational indicia on an exposed surface of the supply container 22 as generaly indicated in FIG. 5 as 40. The informational indicia 40 provides certain instruction as generally indicated as 42 for the proper operation of the irrigating apparatus as well as a quantity measuring gauge or indicator generally indicated as 44 and further a level indicator structure generally indicated as 46. In the proper operation of the subject irrigating apparatus, and to accomplish efficient irrigation of the colon of the patient, it is best for the supply container 22 to be positioned along the length of the respective base segmen 14 such that the container 22 is substantially at eye level with the patient or user of the irrigating apparatus.

This is readily accomplished due to the versatile structural components of the subject mounting assembly 10 through the provision of the aforementioned first connecting element 20 adjustably mounted to travel along the length of the corresponding base segment 14 and more specifically the channel or track segment 18. The supply container 22 can thereby be located at virtually any position through the selective positioning of the first connecting element 20 at the proper "height" or location along the corresponding base segment 14 on which the supply container is movably supported.

Figure 8:
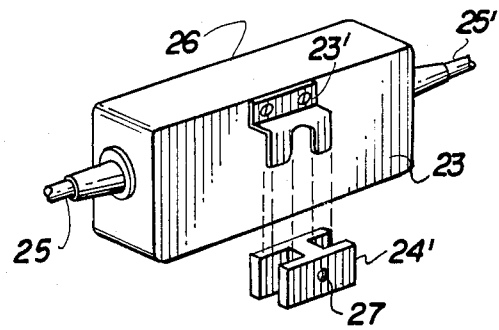
FIG. 8 is a perspective view of one embodiment of a monitoring device of the irrigating apparatus of the present invention shown in partial cutaway and further showing in detail and partially exploded form a connecting member for such monitoring device.

With reference to FIGS. 2, 4 and 8, the monitoring device 26' is similarly selectively positionable along the length of the corresponding base segment 14. For most efficient operation, the monitoring device 26 or 26', depending upon the embodiment utilized, may also be located at a preferred location along the length of the corresponding base segment 14. This selective positioning and movement is accomplished by the provision of a second connecting element 24' (see FIG. 8) which removably engages the rear surface 23 of the monitoring device 26' due to the inclusion thereon of a hook type bracket 23'. The second connecting element 24' is removably secured to the bracket 23' as shown in FIG. 8 and is also capable of being mounted within the track segment or channel 18 associated with the corresponding base segment 14. While the second connecting element 24' is shown with use in combination with the embodiment 26' of the monitoring device, it should be readily apparent that the same connecting element 24' or a structural modification thereof may also be used to movably and selectively position and support the monitoring device 26 as shown in FIG. 3.

Further with regard to the first connecting element 20 (FIGS. 2 through 4) and the second connecting element 24 (FIG. 8), both may be attached to the appropriate channel 18 such as shown in FIGS. 2 and 4. Such attachment is accomplished by the provision of a connector generally of the type 55 shown in FIG. 7 or 55' shown in FIG. 13. More specifically, an aperture 27 is extended into the interior of the second connecting element 24' as shown in FIG. 8 and a similar aperture (not shown) in the rear surface of the first connecting element 20. Such a connector as 55 or 55' includes an enlarged portion such as an enlarged head or skirt as shown, respectively on the referred to connectors 55 and 55'. Such enlarged portion is of greater transverse dimension than that of channel 18 of FIGS. 2 through 4. The elongated peripheral borders of channel 18 will then be clamped and fixed between the connector and the respective first or second oonneoting element when the connector is tightened. However, the first or second connecting element will be allowed to move along the length of the applicable channel 18 when the connector 55 or 55', or a structural equivalent thereof, is loosened somewhat from the first or second connecting element.

Finally, with regard to FIGS. 2, 3, 4, 6 and 7, the base comprising both base segments 14 is best supported or maintained in a substantially vertical upright position. In order to accomplish this, a support means is used to mount and/or support the base on a variety of support structures.

Figure 13:
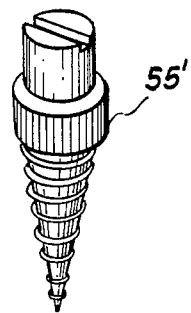
FIG. 13 is a perspective view of another embodiment of a connector element of the type used to attach a mounting assembly to a wall or alternately a connecting element to a base of the subject assembly.

As shown in FIG. 2, support means 50 comprises a bracket 52 having at least one but preferably a plurality of spaced apart hook elements 54 secured to an uppermost opposite longitudinal end of the base by a conventional connector element such as a screw or the like as designated in FIG. 7 as 55. With reference to FIG. 13, a screw 55' could also be used to connect the base in this fashion. The bracket, as also demonstrated in FIG. 1, allows for the depending vertical and substantially upright orientation of the base by movably engaging the bracket 52 with a horizontally oriented support rod or bar such as used to support shower curtains in the conventional fashion. The rod 59 must be of sufficient strength and rigidity to support the irrigating apparatus on the mounting assembly 10 in the manner shown.

Figure 6:
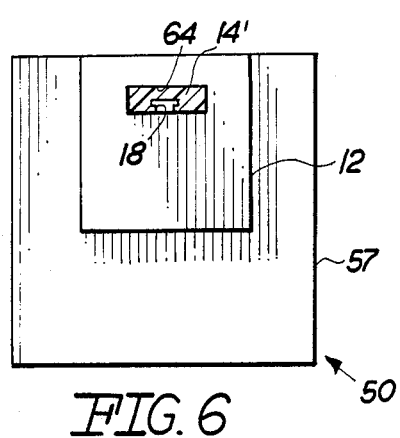
FIG. 6 is a sectional view along line 6—6 of FIG. 3.

With reference to FIGS. 1, 3 and 6, another embodiment of the support means is indicated as 50' and includes a support platform 57 having an undersurface 60 designed to be positioned on a substantially disposed supporting surface as shown clearly in FIG. 1. The support platform 57 has an upper plate or rising portion 62 with an aperture or channel 64 integrally formed therein. The channel is of sufficient depth and overall dimension and configuration to receive the lowermost end as at 14' of the base therein for upstanding vertical support as shown in FIGS. 1 and 3.

Finally with regard to FIGS. 1 and 4, a third embodiment of the support means is the provision of apertures in opposite longitudinal ends of the base or the corresponding longitudinal base segments and as indicated as 50". Appropriate apertures are provided and indicated as 67 for the receipt of conventional connector elements such as screws, nails, etc. and indicated as 69. In this embodiment, the base is substantially semi-permanently secured to the outer wall surface again in the manner clearly represented in FIG. 1.

Convenience in the structure and design of the subject mounting assembly is apparent in that the base segment 14 can be readily separated from one another for storage in a small area or ease of transport. Also, the various embodiments of the support means 50, 50' and 50" may be substantially removed or disassembled to facilitate the aforementioned storage or transportation.

It is therefore to be understood that the following claims are intended to cover all of the generic and specific features of the subject invention herein described, and all the statements of the scope of the invention which as a matter of language, might be said to fall therebetween.

Now that the invention has been described, what is claimed is:

1. In combination, a mounting assembly and an intestinal irrigation apparatus being supported thereon, wherein said intestinal irrigation apparatus comprises a supply container means for storing and dispensing irrigating liquid, a flow indicating monitor means for indicating fluid flow from said supply container to a patient, introduction means mounted on a patient for directing flow into an intestine entrance and a conduit means serving to channel flow of the irrigating fluid from the supply container means to the flow monitor means and subsequently therefrom to the introduction means and into the intestine entrance; said mounting assembly comprising:
   (a) a base having an elongated configuration and comprising two elongated separably connected based segments attached in colinear relation to one another,
   (b) each of said base segments terminating in opposite longitudinal ends and correspondingly positioned longitudinal ends of said base segments removably secured to one another,
   (c) a support means for connecting said base on a support structure in a substantially upright orientation and being secured to a free one of said opposite ends of said base segments when said base segments are connected to one another, said support means disposed outwardly from said base into engagement with the supporting structure,
   (d) a first connecting element disposed and structured for removable support of said supply container means and a second connecting element disposed and structured for removable support of said monitoring means, both said first and second connecting elements mounted on said base and cooperatively structured therewith for selective positioning along at least a portion of the length thereof in spaced relation to one another,
   (e) a track means comprising two track segments each formed in a separated one of said base segments, each track segment comprising a channel integrally formed in one of said base segments,
   (f) each of said base segments comprising a substantially flat configuration extending along its length and each of said channels extending transversely through a different one of said base segments to facilitate adjustable mounting or one of said first or second connector elements thereto, and
   (g) said base segments and said connecting elements cooperatively structured and dimensioned for depending disposition of said conduit means of the irrigation device from said base into engageable relation with said introduction means and a patient.

2. An assembly as in claim 1 wherein said introduction means comprises an introducing element having a substantially continuous smooth outer surface being configured and dimensioned for placement of said introducing element into the intestine entrance, a distal end of said introducing element comprising a plurality of spaced apart channels extending between said outer surface and a hollow interior portion of said introducing element, said conduit connected to said introducing element and said hollow interior portion in fluid communication therewith, whereby the irrigating fluid passes from said conduit into said hollow interior portion and through said channel into said intestine.

3. An assembly as in claim 1 wherein said supply container comprises indicator structure formed thereon and positioned for visual observation by the user, said indicator structure disposed on said supply container for proper positioning of said supply container along the length of said base in aligned relation to the eye level of the user during use of the irrigating apparatus.

4. In combination, a mounting assembly and an intestinal irrigation apparatus being supported thereon, said intestinal irrigation apparatus comprising,
   a supply container means for storing and dispensing irrigating liquid,
   a flow indicating monitor means for indicating fluid flow from said supply container to a patient,
   introduction means to direct fluid flow into an intestinal entrance of a patient, and
   conduit means serving to channel flow of the irrigating fluid from the supply container means to the flow monitor means and subsequently therefrom to the introduction means and into the intestine entrance, said mounting assembly comprising,
   an elongate standard having an upper end and a lower end,
   support means on the standard to maintain the standard in an upright attitude,
   a first connecting element and a second connecting element each including means to position the elements on the standard in spaced relation from one another, said first connecting element comprising means to connect said container means adjacent the upper end of said standard, and said second connecting element comprising means to attach said flow indicating monitor means to said standard below said first connector means, and said standard and said connecting elements cooperatively structured and dimensioned for depending disposition of the conduit of the irrigating device from said standard into engagable relation with a user thereof.

5. The combination as set forth in claim 4 wherein said standard includes guide means extending along at least a portion of the length thereof for guiding movement and selective placement of said first connecting element to adjust the height of said supply container means.

6. The combination as set forth in claim 5 wherein said guide means is dimensioned to extend along at least a major portion of the length of said standard, and said first and second connector elements being movably secured to said standard and movable along at least a portion of said guide means.

7. The combination as set forth in claim 4 wherein said standard includes a first and a second elongate segments and means to secure the segments together in colinear end-to-end relation.

* * * * *